US00PP20524P2

(12) United States Plant Patent
Elfers et al.

(10) Patent No.: US PP20,524 P2
(45) Date of Patent: Dec. 8, 2009

(54) ***CUCURBITA* VARIETY PLANT NAMED 'ANYTIME SQUASH'**

(50) Latin Name: *Cucurbita quisquam*
Varietal Denomination: Anytime Squash

(76) Inventors: Elke Elfers, 3298 Farm Rd., 1158, Clarksville, TX (US) 75426; Urusla Elfers, 3298 Farm Rd., 1158, Clarksville, TX (US) 75426

( * ) Notice: Subject to any disclaimer, the term of this patent is extended or adjusted under 35 U.S.C. 154(b) by 98 days.

(21) Appl. No.: 11/727,000

(22) Filed: Mar. 23, 2007

(51) Int. Cl.
*A01H 5/00* (2006.01)

(52) U.S. Cl. ..... Plt./258

(58) Field of Classification Search ..... Plt./258
See application file for complete search history.

*Primary Examiner*—Annette H Para
(74) *Attorney, Agent, or Firm*—Michael L. Diaz

(57) ABSTRACT

A variety of *Cucurbita quisquam* squash having a sprawling vine bearing squash fruit.

6 Drawing Sheets

Latin name of the genus and species of the plant claimed: *Cucurbita quisquam.*

Field of the Invention

This invention relates to a new and distinctive cultivar that is botanically known as *Cucurbita quisquam* squash.

SUMMARY OF THE INVENTION

The present invention relates to a new and distinct *Cucurbita* cultivar that is botanically known as *Cucurbita quisquam* squash.

The parentage of the new cultivar may be summarized as follows:

*Cucurbita* cylindrical (zucchini)×*Cucurbita* pepo (pumpkin)×unknown

DESCRIPTION OF THE INVENTION

The *Cucurbita quisquam* squash has not been observed under all possible environmental conditions. The following observations and descriptions are of a plant grown outside in Clarksville, Tex.

The parents are zucchini, pumpkin and an unknown plant.

The *Cucurbita quisquam* squash has a growth habit and cultivation similar to the vine varieties like pumpkin and zucchini squash. It can grow on vines that typically fall in the range of 8 to 20 feet long with a plurality of the fruit (squash) located on the vines. Additionally, the vines include broad green leaves.

The fruit are cylindrical to pear-shaped. The fruit, at 4 weeks old range in size between 2 to 4 inches in length. The fruits resemble zucchini at 4 weeks old. Later, at several months, the fruit is a large, yellow squash of about 6–8 inches in length. At full maturity, the fruit is about 8–10 inches to 24 inches. The mature squash is light orange. The squash has a plurality of nodules on the surface of the fruit. The flesh of the fruit is creamy white at 4 weeks. Later in the fruit's maturity, the color is light gold. At The skin of the fruit at its early stages is similar to a zucchini. As the fruit matures, it is thicker like winter squash with an orange color.

Figure 1:
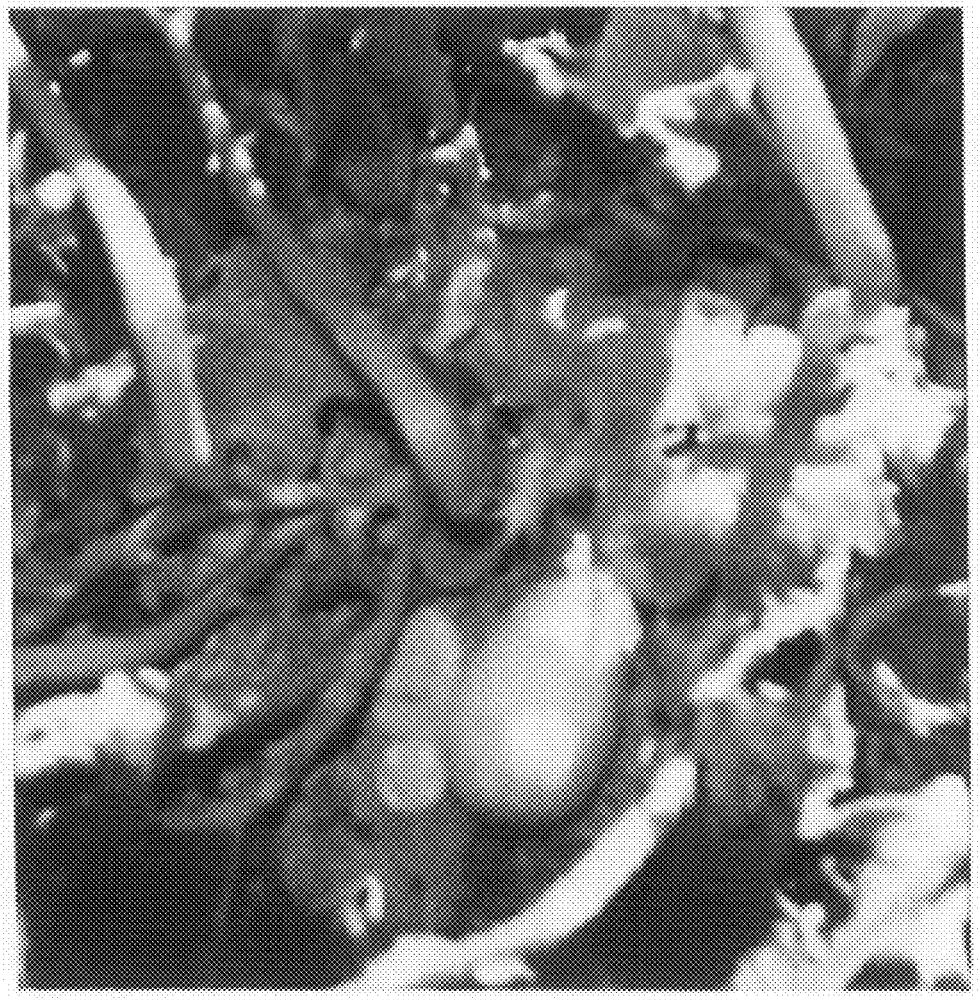
FIG. 1 shows a vine and squash.
Figure 2:
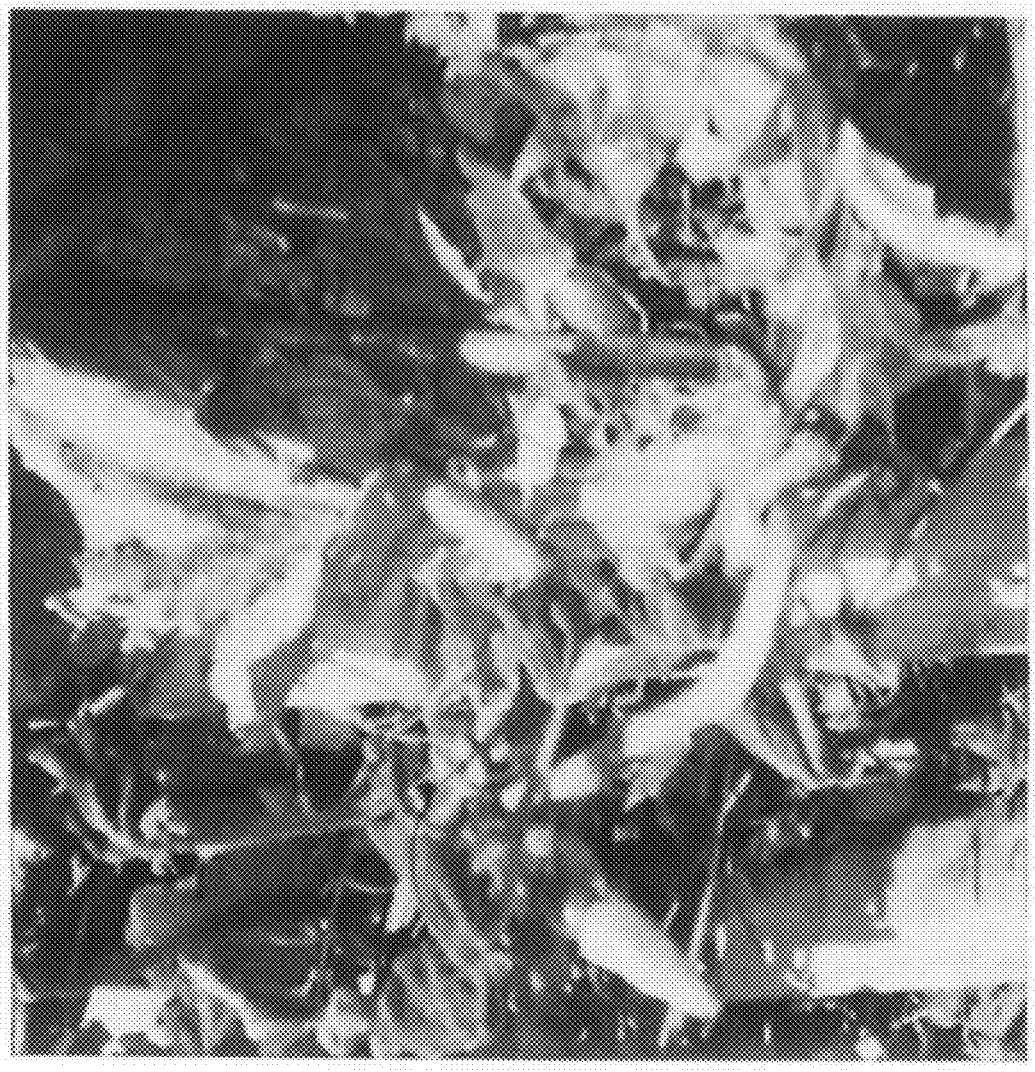
FIG. 2 shows the vine and foliage of the plant.
Figure 3:
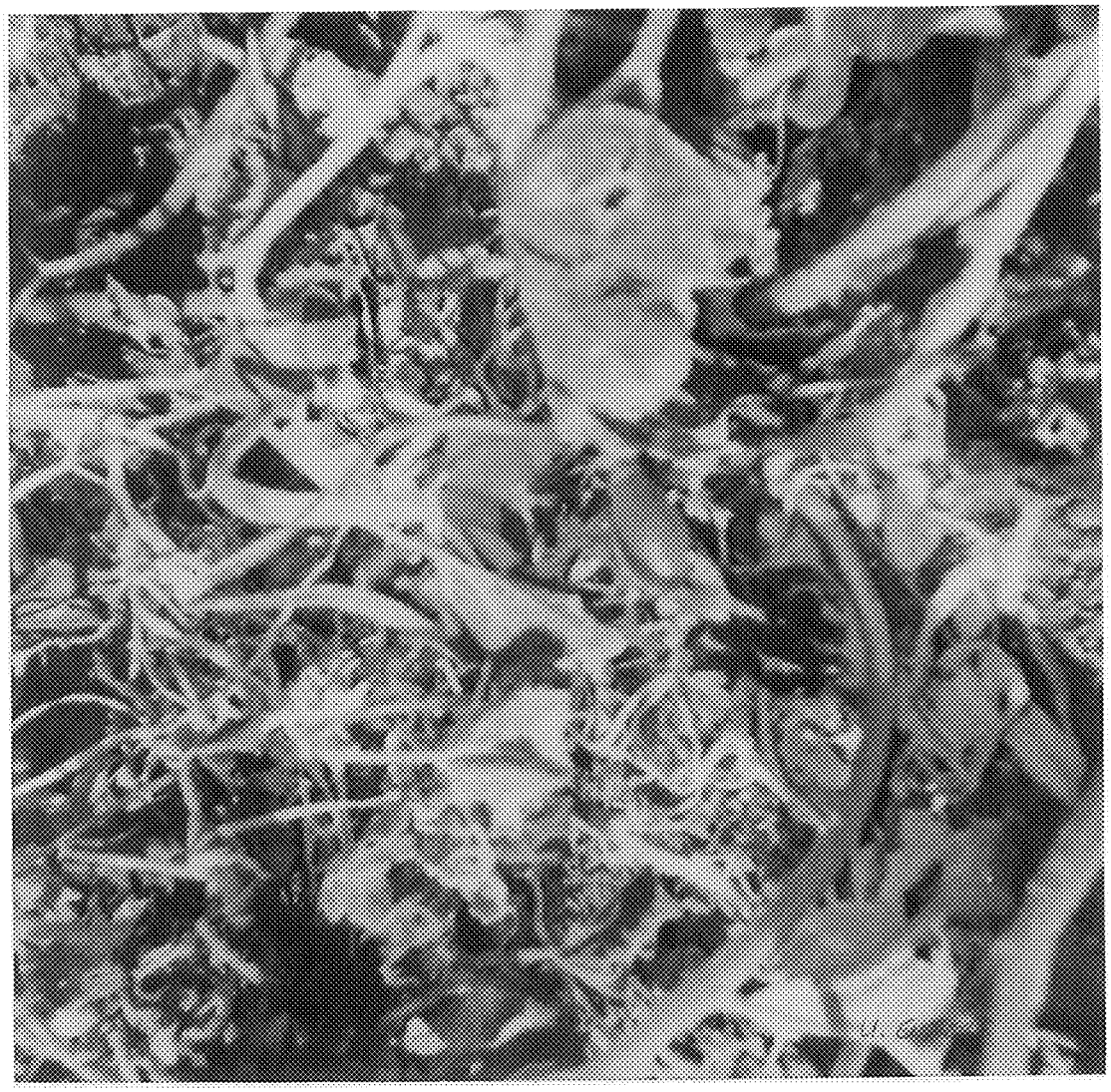
FIG. 3 illustrates the vine and squash of the plant shortly after fertilization.
Figure 4:
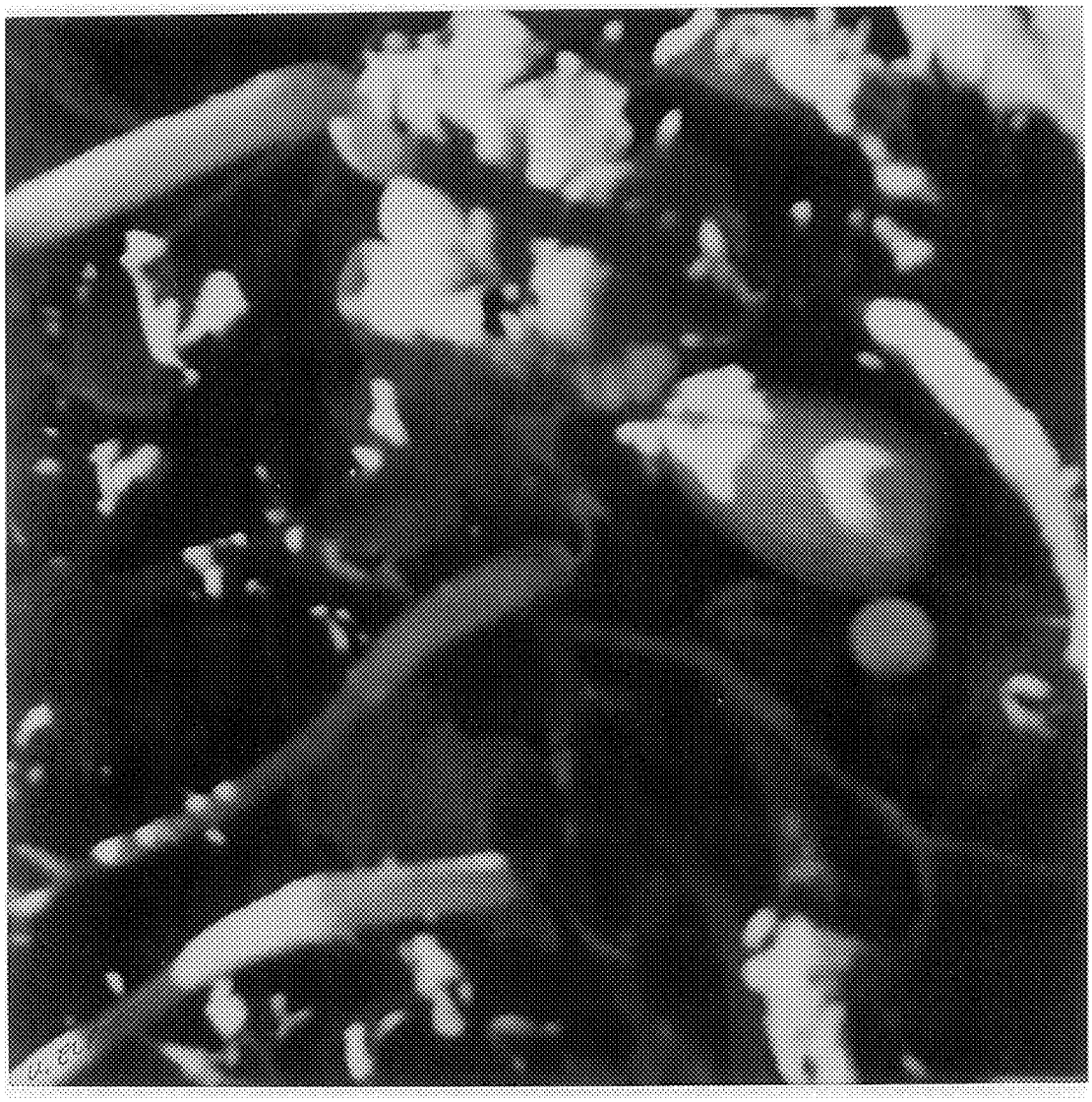
FIG. 4 illustrates the squash developing on the vine of the squash.
Figure 5:
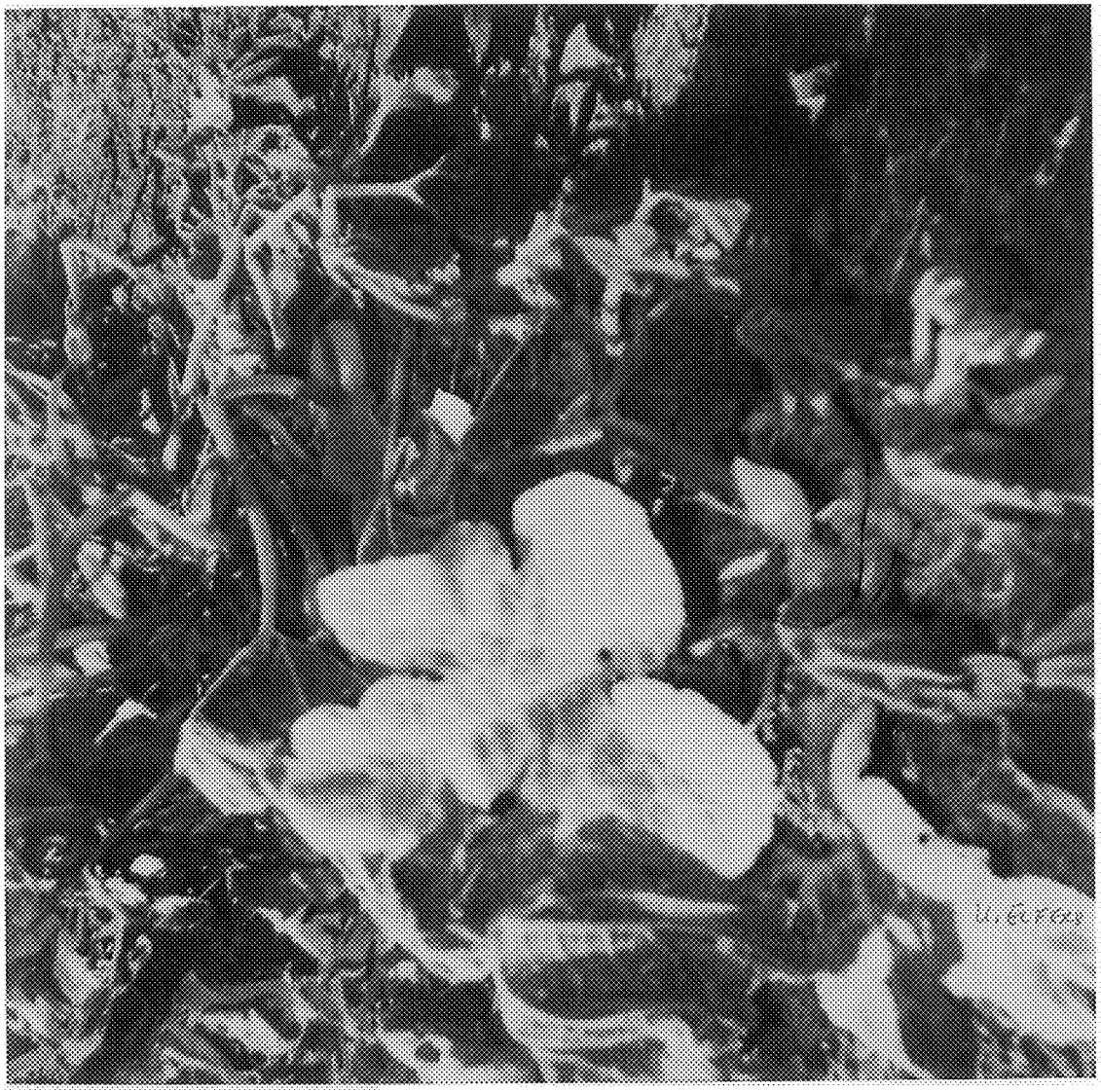
FIG. 5 illustrates the squash, leaf, vine and bud of the plant after a first frost.
Figure 6:
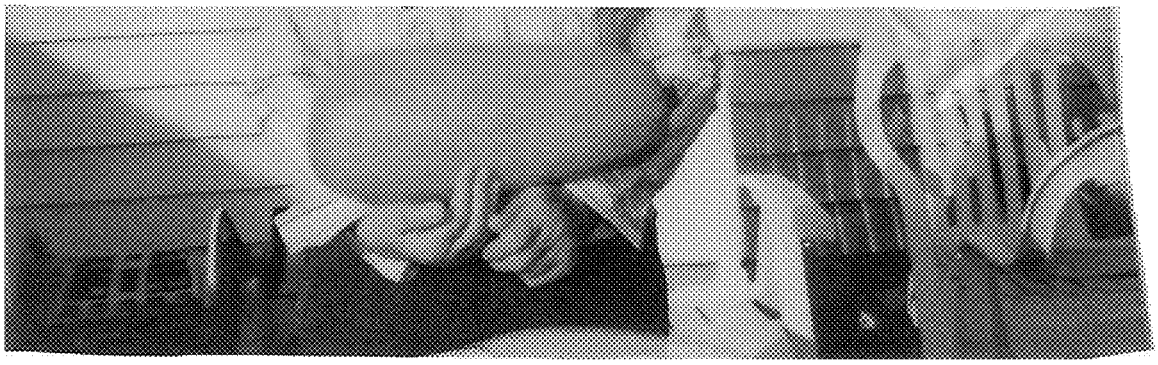
FIG. 6 illustrates a harvest fully mature squash from the plant.

The plant was first asexually propagated by vegetative cutting in 2005 near Clarksville, Tex. The mature plant in FIG. 6 is approximately seventy days. In regards to the growing conditions of the plant, the plant began after the last frost of the winter, when soil warms (approximately the month of April). The plant is grown in full sun, brown to black soil, medium to heavy soil with some humus mixed in and fertilized with 5-10-5 fertilizer. Later in the growing cycle, organic fertilizer in hills about 4 to 6 feet apart was applied to the plant. The plant thrived in the rainy season. During the dry summer months in hot weather (e.g., 100 degrees Fahrenheit), the plant requires watering every other day. The color of the leaves varies with maturity. New leaves have an upper side of a moderate yellowish green near 136C and a lower side of strong yellowish green near 144A. For mature leaves, the upper side is moderate yellowish green near 139D and a lower side of light yellowish green near 145C.

There are several differences between parents and related (similar cultivars). The fruit (squash) is squash shaped. The squash changes as it matures and is stored. The squash keeps a long time after being harvested (i.e., over sixty days). The plant germinates about 7–10 days and grows rapidly. The squash is about an inch when fertilization occurs and can be eaten anytime from then until squash reaches its final maturation (i.e., sixty or more days).

In regards to cold and drought resistance of the plant, after the last frost free date in spring, the plant may be started. The plant may also be started indoors earlier and transferred outside. If sheltered, the plant can survive the first light frost. In this situation, the top outer leaves get burned, but the stems remain intact and leaves under outside leaves remain intact. The squash thrives in warm weather and grows prolifically in spring rains and keeps growing in the hot July and August weather, if is watered every week. In 105 degree Fahrenheit tempter, watering is necessary every day or every other day.

In regards to diseases and inserts, the biggest problem is the "squash bug". It takes a lot of these insects to weaken or kill the plant. The branching habit helps the plant to survive pests such as the squash bug. In some locations, mildew can affect the plant, in particular upon the leaves. This usually occurs in partial shade, but because the branches form from the vine, another branch of the vine may survive.

The plant grows quickly and has a leaf span of about 6 to 8 inches across and about 8 to 10 inches long. The plant makes long vines that branch. Some of the branches secure themselves in the ground after a period of time. If the vines are cut, the branches re-grow. In addition, the plant has flowers. The squash can be eaten at various stages of development, form the small fertilized fruit of 1 to 3 inches, until totally mature. When harvested in the fall, the squash has a hard skin, similar to a winter squash and has a color of moderate yellow near 162B. Earlier in the season, the squash is similar to a summer squash, with a soft skin which easily peels. It slices easily and has a pale yellow color (near 158B) flesh inside. The interior of the squash becomes more golden as it matures and is stored.

What is claimed is:

1. A new and distinct variety of *Cucurbita quisquam* squash plant names 'anytime squash' substantially as illustrated and described.

* * * * *